United States Patent
Milius et al.

(10) Patent No.: US 6,667,396 B2
(45) Date of Patent: Dec. 23, 2003

(54) POLYXYLOSIDE DERIVATIVES, PROCESS FOR PREPARING THEM, COMPOSITION CONTAINING THEM AND USE AS SURFACTANTS

(75) Inventors: Alain Milius, Nice (FR); Jean-Pierre Boiteux, Saix (FR); Hervé Rolland, Castres (FR); Guy Tabacchi, Castres (FR)

(73) Assignee: Societe d'Exploitation de Produits pour les Industries Chimiques Seppic, Paris Cedex (FR)

( * ) Notice: Subject to any disclaimer, the term of this patent is extended or adjusted under 35 U.S.C. 154(b) by 118 days.

(21) Appl. No.: 09/826,964

(22) Filed: Apr. 6, 2001

(65) Prior Publication Data

US 2001/0039337 A1 Nov. 8, 2001

(30) Foreign Application Priority Data

Apr. 6, 2000 (FR) .............................. 0004414

(51) Int. Cl.$^7$ .......................... C07H 15/04; C11D 3/22
(52) U.S. Cl. .................. 536/123.1; 536/18.6; 536/120; 536/124
(58) Field of Search .............................. 536/123.1, 124, 536/18.6, 120

(56) References Cited

U.S. PATENT DOCUMENTS

| 5,681,949 A | 10/1997 | Johansson et al. |
| 6,495,147 B1 * | 12/2002 | Dumas et al. |

FOREIGN PATENT DOCUMENTS

| DE | 43 11 159 | 10/1994 |
| EP | 0 092 355 | 10/1983 |
| EP | 0 387 912 | 9/1990 |

* cited by examiner

Primary Examiner—Samuel Barts
Assistant Examiner—Michael C. Henry
(74) Attorney, Agent, or Firm—Young & Thompson

(57) ABSTRACT

Novel compounds of formula (I):

$$RO-(X)_p \qquad (I)$$

in which
p represents a decimal number between 1 and 5,
x represents a xylose residue, and
R represents a radical:

$$CH(C_nH_{2n+1})(C_mH_{2m+1})-CH_2-$$

in which m is an integer between 6 and 18, n is an integer between 4 and 18 and the sum n+m is greater than or equal to 10. Process for preparing them, compositions containing them and their use as surfactants.

17 Claims, No Drawings

POLYXYLOSIDE DERIVATIVES, PROCESS FOR PREPARING THEM, COMPOSITION CONTAINING THEM AND USE AS SURFACTANTS

BACKGROUND OF THE INVENTION

The present invention relates to novel compounds derived from sugar, to processes for preparing them and to their uses as surfactants.

During its research directed towards preparing surfactants capable of producing vesicular emulsions or inverse micelles, the Applicant noted that some of these bicatenary compounds made it possible to produce emulsions of this type.

SUMMARY OF THE INVENTION

Accordingly, a subject of the invention is a compound of formula (I):

$$RO—(X)_p \quad (I)$$

in which:
p represents a decimal number between 1 and 5 and
X represents a xylose residue, and
R represents a branched alkyl radical:

$$CH(C_nH_{2n+1})(C_mH_{2m+1})—CH_2—$$

in which m is an integer between 6 and 18, n is an integer between 4 and 18 and the sum n+m is greater than or equal to 10.

The oligomeric structure $(X)_p$ may be in any isomeric form, whether of optical isomerism, geometrical isomerism or positional isomerism; it may also be a mixture of isomers.

In formula (I), the group R—O— is linked to X by the anomeric carbon of the saccharide residue, so as to form an acetal function.

p, which represents the average degree of polymerization of the saccharide, is more particularly between 1 and 2.5 and most particularly between 1 and 2.0.

DESCRIPTION OF THE PREFERRED EMBODIMENTS

According to a first particular aspect of the present invention, one subject thereof is a compound of formula (I), as defined above, in which n and m are even numbers.

According to a second particular aspect of the present invention, a subject thereof is a compound of formula (I), as defined above, in which the sum n+m is equal to 10. In this case, R more particularly represents a 2-butyloctyl radical (n=4, m=6).

According to a third particular aspect of the present invention, a subject thereof is a compound of formula (I), as defined above, in which the sum n+m is equal to 12. In this case, R more particularly represents a 2-butyldecyl radical (m=4, n=8) or a 2-hexyloctyl radical (m=6, n=6).

According to a fourth particular aspect of the present invention, a subject thereof is a compound of formula (I), as defined above, in which the sum n+m is greater than or equal to 14. In this case, R more particularly represents a 2-hexyldecyl radical (n=6, m=8), a 2-hexyldodecyl radical (m=6, n=10), a 2-octyldecyl radical (m=8, n=8), a 2-octyldodecyl radical (m=8, n=10), a 2-decyltetradecyl radical (m=10, n=12), a 2-dodecylhexadecyl radical (m=12, n=14), a 2-tetradecyloctadecyl radical (m=14, n=16), a 2-tetradecyleicosyl radical (m=14, n=18), a 2-hexadecyloctadecyl radical (m=16, n=16) or a 2-hexadecyleicosyl radical (m=16, n=18).

A subject of the invention is also a process for preparing a compound of formula (I) as defined above, characterized in that the xylose of formula (II):

$$HO—X \quad (II)$$

is reacted with an excess of alcohol of formula (III):

$$ROH \quad (III)$$

to form, after removal of the unreacted fatty alcohol of formula (III), the compound of formula (I).

In the process as defined above, the reaction for formation of the compound of formula (III) is carried out in the presence of strong acid catalysts such as, for example, mineral acids, for instance sulphuric acid or hypophosphorous acid or a mixture of these acids.

According to one variant of the process as defined above, the xylose of formula (II) is reacted with an alcohol of formula (IV):

$$R_1—OH$$

in which $R_1$ contains from 1 to 4 carbon atoms, and more particularly with butanol, to give the acetal of formula (V):

$$R_1O—(X)_p \quad (V),$$

this acetal of formula (V) then undergoing a transacetalization with an excess of alcohol of formula (III) with distillation of the alcohol of formula (IV) formed, followed by removal of the unreacted alcohol of formula (III).

In the process and its variant, as described above, the removal of the unreacted alcohol of formula (III) is carried out according to methods that are known to those skilled in the art, such as, for example, distillation, thin-film distillation, molecular distillation or solvent-extraction.

The compound of formula (V) by itself constitutes another aspect of the present invention.

According to another aspect of the present invention, a subject thereof is a composition (A), consisting of a mixture of at least two compounds of formula (I) which may be obtained by the process or its variant as are defined above, using a mixture of alcohols of formula (III) instead of only one of these alcohols of formula (III).

According to another aspect of the present invention, a subject thereof is a composition (B), characterized in that it comprises:
more than 0% by weight and less than 100% by weight, preferably from 1% to 60% by weight, of a compound of formula (I) or of a mixture of compounds of formula (I), as defined above, and
more than 0% by weight and less than 100% by weight, preferably from 40% to 99% by weight, of a compound of formula (III) or of a mixture of compounds of formula (III), as defined above.

The composition B as defined above is prepared, for example, by reacting an excess of compounds of formula (III) with xylose according to the process or its variant as are defined above, without removal of the unreacted alcohols of formula (III). It may also be obtained by mixing an alcohol of formula (III) or a mixture of alcohols of formula (III) with a compound of formula (I) or a mixture of compounds of formula (I).

The chain(s) R of the compound(s) of formula (III) is (are) preferably identical to those of the compound(s) of formula (I).

According to a final aspect of the present invention, a subject thereof is the use of a compound of formula (I), of a composition (A) or of a composition (B), as described above, as a surface agent or surfactant, and more particularly the use as an emulsifier when the sum n+m is greater than or equal to 14 and as a foaming agent, wetting agent, detergent agent or antifoam solubilizing agent, when the sum n+m is less than 14.

The examples which follow illustrate the invention without, however, limiting it.

EXAMPLE 1

Acetalization of Xylose with Isofol™18 in Excess (Composition $B_1$)

A mixture of alcohols mainly comprising 2-hexyldodecanol and 2-octyldodecanol, sold under the name Isofol™18, is heated to 90° C. in a reactor, followed by addition, with stirring, of xylose in a xylose/alcohols stoichiometric ratio=1/6, and the mixture is left to react for 4 hours in the presence of an acid catalyst. After cooling, neutralization and filtration, a mixture $B_1$ of xylosides and of fatty alcohols, which is relatively uncoloured and which corresponds to the characteristics below, is obtained:

| | |
|---|---|
| Acid number ($I_A$) | 0.05 |
| Hydroxyl number ($I_{OH}$) | 241.5 |
| Content of free alcohols in the final mixture $B_1$: | 84.9% |
| Content of alkyl polyxylosides in the final mixture $B_1$: | 15.1% |

EXAMPLE 2

Acetalization of Xylose with Isofol™12

744 g of 2-butyloctanol, sold under the name Isofol™12, are heated to 65° C. in a reactor, followed by addition, with stirring, of 150 g of xylose, and the mixture is left to react for 6 hours at about 100° C. under partial vacuum, in the presence of an acid catalyst. After cooling, neutralization and filtration, the excess Isofol™12 is distilled off to give a foaming surfactant corresponding to a product of formula (I), as defined above, in which R represents a 2-butyloctyl radical.

EXAMPLE 3

Acetalization of Xylose with Isofol™36 (Composition $B_2$)

Excess butanol and xylose are mixed together with stirring in the presence of an acid catalyst at 100° C. under reduced pressure so as to evaporate off the water formed. After two hours, an excess of Isofol™36, which consists mainly of 2-hexadecyleicosanol (m=16, n=18), is added and the mixture is left to react for 7 hours, distilling off the butanol released. After cooling, neutralization and filtration, an emulsifying surfactant corresponding to a composition B as defined above is obtained, comprising about 60% free 2-hexadecyleicosanol and about 40% of a product of formula (I) in which R represents a 2-hexadecyleicosyl radical (composition $B_2$).

Preparation of a Composition of the Prior Art (Composition $C_1$)

Isofol™18 is heated to 90° C. in a reactor, followed by addition, with stirring, of glucose in a glucose/alcohols stoichiometric ratio=1/6, and the mixture is left to react for 4 hours in the presence of an acid catalyst. After cooling, neutralization and filtration, a mixture $C_1$ of alkylglucosides and of fatty alcohols is obtained.

Emulsion Stability Study

Emulsions $E_1$, $E_2$ and $E_3$ are prepared, with the composition $B_1$ of Example 1 as emulsifier, and emulsions $F_1$, $G_1$, $F_2$, $G_2$, $F_3$ and $G_3$ are prepared, with the composition $C_1$ as emulsifier, by simple hot-mixing of the various constituents.

It is observed that the emulsions $E_1$ to $E_3$ prepared with the composition according to the invention are more stable than the emulsions prepared with the same concentration of composition $C_1$ of the prior art.

The results are given in the table below (the result ++ indicates that no phase separation was observed after the emulsion was maintained at 40° C. for one month. The result − indicates that a phase separation of the emulsion was observed after two weeks at 40° C.): stable after:

| Constituents | Emulsions | | | | | | | | |
|---|---|---|---|---|---|---|---|---|---|
| (% by weight) | $E_1$ | $F_1$ | $G_1$ | $E_2$ | $F_2$ | $G_2$ | $E_3$ | $F_3$ | $G_3$ |
| $B_1$ | 3 | 0 | 0 | 3 | 0 | 0 | 3 | 0 | 0 |
| $C_1$ | 0 | 3 | 5 | 0 | 3 | 5 | 0 | 3 | 5 |
| Primol ™ 352 | 5 | 5 | 5 | 0 | 0 | 0 | 0 | 0 | 0 |
| Trigly ™ 5545 | 0 | 0 | 0 | 5 | 5 | 5 | 0 | 0 | 0 |
| Lanol ™ 99 | 0 | 0 | 0 | 0 | 0 | 0 | 5 | 5 | 5 |
| Simulgel ™ EG | 1 | 1 | 1 | 1 | 1 | 1 | 1 | 1 | 1 |
| Water | qs | qs | qs | qs | qs | qs | Qs | qs | qs |
| Preserving agent | qs | qs | qs | qs | qs | qs | Qs | qs | qs |
| Stability at 40° C. | ++ | − | ++ | ++ | − | ++ | ++ | − | ++ |

This result indicates that stable emulsions may be prepared, using a smaller amount of emulsifying alkylpolyxylosides than of emulsifying alkylpolyglucosides.

What is claimed is:

1. Compound of formula (I):

$$RO\text{—}(X)_p \quad (I)$$

in which:

p represents a decimal number between 1 and 5 and

X represents a xylose residue, and

R represents a branched alkyl radical:

$$CH(C_nH_{2n+1})(C_mH_{2m+1})\text{—}CH_2\text{—}$$

in which m is an integer between 6 and 18, n is an integer between 4 and 18 and the sum n+m is greater than or equal to 12.

2. Compound of formula (I) as defined in claim 1, in which p, which represents the average degree of polymerization of the saccharide, is between 1 and 2.5.

3. Compound of formula (I) as defined in claim 1, in which n and m are even numbers.

4. Compound of formula (I) as defined in claim 1, in which the sum n+m is equal to 12.

5. Compound of formula (I) as defined in claim 4, in which R represents a 2-butyldecyl radical or a 2-hexyloctyl radical.

6. Compound of formula (I) as defined in claim 1, in which the sum n+m is greater than or equal to 14.

7. Compound of formula (I) as defined in claim 6, in which R represents a 2-hexyldecyl radical, a 2-hexyldodecyl radical, a 2-octyldecyl radical, a 2-octyldodecyl radical, a 2-decyltetradecyl radical, a 2-dodecylhexadecyl radical, a 2-tetradecyloctadecyl radical, a 2-tetradecyleicosyl radical, a 2-hexadecyloctadecyl radical or a 2-hexadecyleicosyl radical.

8. Process for preparing a compound of formula (I) as defined in claim 1, characterized in that the xylose of formula (II):

$$HO-X \qquad (II)$$

is reacted with an excess of alcohol of formula (III):

$$ROH \qquad (III)$$

to form, after removal of the unreacted fatty alcohol of formula (III), the compound of formula (I).

9. The process as defined in claim 8, in which the xylose of formula (II) is reacted with an alcohol of formula (IV):

$$R_1-OH$$

in which $R_1$ contains from 1 to 4 carbon atoms, to give the acetal of formula (V):

$$R_1O-(X)_p \qquad (V)$$

this acetal of formula (V) then undergoing a transacetalization with an excess of alcohol of formula (III) with distillation of the alcohol of formula (IV) formed, followed by removal of the unreacted alcohol of formula (III).

10. Composition (A), consisting of a mixture of at least two compounds of formula (I) as defined in claim 1, which may be obtained by reacting xylose with a mixture of alcohols of formula (III).

11. Composition (B), characterized in that it comprises:
more than 0% by weight and less than 100% by weight of a compound of formula (I) or of a mixture of compounds of formula (I), as defined in claim 1, and
more than 0% by weight and less than 100% by weight of a compound of formula (III) or of a mixture of compounds of formula (III).

12. The method of using a compound of formula (I), as defined in claim 1, as a surface agent or surfactant, comprising the step of adding the compound of formula (I) to a mixture, wherein the compound of formula (I) is added as a surface agent or surfactant.

13. The method of using a compound of formula (I), as defined in claim 1, comprising the step of adding the compound of formula (I) to a mixture, wherein in the compound of formula (I) the sum n+m is greater than or equal to 14, and the compound of formula (I) is added as an emulsifier.

14. The method of using a compound of formula (I), as defined in claim 1, comprising the step of adding the compound of formula (I) to a mixture, wherein in the compound of formula (I) the sum n+m is less than 14, and the compound of formula (I) is added as a foaming agent, wetting agent, detergent or antifoam solubilizing agent.

15. Compound of formula (I) as defined in claim 1, in which p, which represents the average degree of polymerization of the saccharide, is between 1 and 2.0.

16. Process of claim 8, wherein the alcohol of formula (IV) is butanol.

17. Composition (B) of claim 11, comprising:
1% to 60% by weight of a compound of formula (I) or of a mixture of compounds of formula (I); and
40% to 99% by weight of a compound of formula (III) or of a mixture of compounds of formula (III).

* * * * *